United States Patent [19]
Mitchnick et al.

[11] Patent Number: 5,756,788
[45] Date of Patent: *May 26, 1998

[54] SILICONE POLYMER-COATED, HYDROPHOBIZED METAL OXIDES

[75] Inventors: Mark A. Mitchnick, Wainscott, N.Y.; Anthony J. O'Lenick, Lilburn, Ga.

[73] Assignees: SunSmart, Inc., Wainscott, N.Y.; Siltech, Inc., Norcross, Ga.

[*] Notice: The term of this patent shall not extend beyond the expiration date of Pat. Nos. 5,565,591 and 5,562,897 and 5,536,492 and 5,486,631.

[21] Appl. No.: 727,714

[22] Filed: Oct. 7, 1996

Related U.S. Application Data

[63] Continuation-in-part of Ser. No. 629,931, Apr. 12, 1996, Pat. No. 5,562,897, which is a continuation-in-part of Ser. No. 549,873, Oct. 30, 1995, Pat. No. 5,536,492, which is a continuation-in-part of Ser. No. 490,494, Jun. 14, 1995, Pat. No. 5,486,631.

[51] Int. Cl.$^6$ ............... A61K 7/112; C07F 3/06; C07F 7/08
[52] U.S. Cl. ............... 556/10; 424/59
[58] Field of Search ............... 556/10; 424/59

[56] References Cited

U.S. PATENT DOCUMENTS

| | | | |
|---|---|---|---|
| 5,380,527 | 1/1995 | Legrow et al. | 424/59 X |
| 5,441,726 | 8/1995 | Mitchnick et al. | |
| 5,447,715 | 9/1995 | Roberts | 424/59 |
| 5,476,643 | 12/1995 | Fogel | 424/59 X |
| 5,486,631 | 1/1996 | Mitchnick et al. | |
| 5,536,492 | 7/1996 | Mitchnick et al. | |
| 5,562,897 | 10/1996 | Mitchnick et al. | |
| 5,565,591 | 10/1996 | Mitchnick et al. | |

*Primary Examiner*—Paul F. Shaver
*Attorney, Agent, or Firm*—Kathleen Madden Williams, Ph.D.

[57] ABSTRACT

A process for making metal oxide hydrophobic by coating the metal oxide with a silicone polymer is disclosed. The hydrophobic metal oxide is prepared by contacting the metal oxide with a reactive silicone compound and then in a subsequent step the coated metal oxide is heated to 40° to 100° C. for between 1 and 10 hours. The resulting metal oxide is hydrophobic, non-reactive, not affected by water and can be applied to the skin for protection from ultraviolet light of the sun.

52 Claims, 1 Drawing Sheet

5,756,788

SILICONE POLYMER-COATED, HYDROPHOBIZED METAL OXIDES

RELATED APPLICATIONS

This application is a continuation in part of U.S. application Ser. No. 08/629,931, filed Apr. 12, 1996, now U.S. Pat. No. 5,562,897, which is a continuation in part of U.S. application Ser. No. 549,873, filed Oct. 30, 1995, now U.S. Pat. No. 5,536,492, which is a continuation in part of U.S. application Ser. No. 490,494 filed Jun. 14, 1995, now U.S. Pat. No. 5,486,631.

This invention relates to metal oxide particles made hydrophobic by a process of coating the metal oxide with a silicone polymer. The hydrophobized metal oxide is prepared by the reaction of a specific type of reactive silicone which is applied to the metal oxide, followed by heating the coated metal oxide to 40° to 100° C. for between 1 and 10 hours for the reaction to occur. The resulting silicone coated metal oxide particles are hydrophobic, non-reactive, and not affected by water. The coated, hydrophobized metal oxides or particles also have a significantly decreased photoreactivity which makes them more resistant to degradation and more chemically inert than non-coated metal oxides. Hydrophobized metal oxides, such as zinc oxide, titanium dioxide and iron oxide, are particularly useful in compositions that are applied to the skin for protection from ultraviolet radiation. Such compositions made according to the invention are effective as delivery systems which produce a uniform hydrophobic film which is not interrupted by extraneous oils, water and other additives which may be in the final formulated product.

DESCRIPTION OF THE ART

Metal oxides, such as zinc oxide, titanium dioxide and iron oxide, are well known compounds that are useful in a variety of applications. For example, titanium dioxide, is used as a pigment in paint, as an additive in cosmetic products, cements, glass, rubber, glue, matches, inks and semiconductors. The use of titanium dioxide in so many application areas is a direct result of the many differing and useful properties of the pigment.

It is very desirable to produce a metal oxide, such as titanium dioxide, which has the pigment properties but lacks the ability to react with other compounds or materials which contact the metal oxide as found in various applications, compositions, or formulations. One area in which metal oxides have been used is in sunscreen products. Metal oxides, such as zinc oxide, titanium dioxide, iron oxide and cesium oxide, can protect the skin from the harmful effects of exposure to the sun. The traditional materials used for protecting the skin from the harmful effect of the sun are the organic sunscreen agents. These include paraamino benzoic acid (PABA) and other materials which absorb ultraviolet light. Recently, studies have indicated that ultraviolet light is a major factor in the aging of skin. This has resulted in the incorporation of sunscreens in products, such as cosmetics, that are not aimed specifically for use as sunscreen compositions. Additionally, there has been an increased interest in providing higher levels of protection to the skin. The so called skin protection factor (SPF) system has been developed to evaluate various materials for their effectiveness in protecting the skin from the damaging effects of the sun. The quest for higher and higher SPF values has resulted in the use of greater levels of organic sunscreens. These materials have a tendency to be irritating at high concentrations and have the effect of increasing the available organic material for bacteria. This in turn results in the need for more preservative to protect the higher level of organic sunscreen agent from bacterial degradation. The higher levels of preservative result in higher irritation levels which can be addressed by incorporation of irritation mitigants which, themselves, are degraded by bacteria.

The use of inorganic sunscreen agents like titanium dioxide is a good way around the use of organic sunscreens since they are not attacked by bacteria. However, their use does have some other inherent problems. Specifically, these materials are not easily formulated into stable products due to the reactivity issues raised above. For example, titanium dioxide tends to agglomerate in many finished formulations, losing its effectiveness in the formulation and resulting in unacceptable aesthetic results, most commonly whitening and viscosity changes. In addition, untreated titanium dioxide reacts with vitamin C in aqueous solution, resulting in a pronounced yellowing of the solution. This is highly undesirable in many cosmetic applications. One approach has been to pre-disperse the titanium dioxide in an organic oil like Siltech's patented tri-(octyldodecyl)-citrate. While the dispersion is fairly stable, the coating is not permanent since there is no reaction between the oil and the titanium dioxide. The oil also disrupts the uniformity of the titanium dioxide on the skin. Traditionally, dispersing aids have been added to formulations to minimize the disruptive effect upon the film. These include phosphate esters and lecithin. These too suffer from the labile nature of the surface treatment and dissociation between the particle and the oil. This is especially evident when titanium dioxide is exposed to extreme mechanical or thermal stress as in the production of plastics or stick cosmetics.

The present invention overcomes the shortfalls of titanium dioxide and other metal oxides by reacting a specific silicone compound under controlled conditions to produce a stable, surface treated metal oxide which maintains its state of dispersion and does not contribute significantly to chemical instability in the formulation.

SUMMARY OF THE INVENTION

The present invention provides processes for making the surface of metal oxides hydrophobic using a specific type of reactive silicone compound, the resulting hydrophobized metal oxides prepared from such processes, and methods for protecting skin from ultraviolet radiation using the hydrophobized metal oxides.

Thus, it is one aspect of this invention to provide a process for hydrophobizing metal oxides comprising contacting the metal oxide with an effective hydrophobizing amount of a silicone compound having the formula:

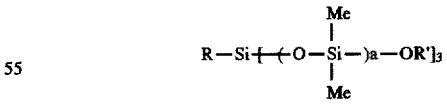

where Me is methyl,

R is alkyl having one to ten carbon atoms,

R' is methyl or ethyl, a is an integer ranging from 4 to 12, and heating the mixture of silicone compound and metal oxide to a temperature of 40° C. to 100° C. for two to ten hours. The effective hydrophobizing amount of silicone compound is defined as that amount of silicone compound which is used to produce a coated, hydrophobized metal oxide particle containing a desired percent, preferably ranging from 0.1 to 25%, by weight of the silicone compound. In one embodiment of the hydrophobizing process, the entire effective hydrophobizing amount of the silicone compound is contacted with the metal oxide at one time and then heated. The metal oxides so produced are referred to as singly-coated metal oxides.

In a more preferred embodiment of the hydrophobizing process of this invention, a portion or increment of the effective hydrophobizing amount of the silicone compound is contacted with the metal oxide followed by heating, and these steps repeated until the entire effective hydrophobizing amount of the silicone compound has been reacted with the metal oxide. As used herein, "portion" refers to a fraction of the total amount which would be applied in a single coating step, and may include, for example, ¼, ½, ¾, etc., where the fraction used in all of the coating steps equals 1. More preferably, the hydrophobizing process is carried out in two successive cycles of mixing one-half of the effective hydrophobizing amount of silicone compound with the metal oxide followed by heating. Metal oxides so produced are referred to as doubly coated metal oxides. Compared to singly coated metal oxides, doubly coated metal oxides have both an advantageously lower photoreactivity, giving the metal oxide an increased stability, and also an enhanced skin protection factor (SPF).

Preferably, applying the effective hydrophobizing amount of silicone compound in the processes of this invention results in a metal oxide having a percent silicone compound ranging from 0.1 to 25% by weight, more preferably 0.5 to 20% by weight, and most preferably 1.0 to 10% by weight.

In another preferred embodiment of this invention, the integer "a" of the structure of the silicone compound used to hydrophobize metal oxides ranges from 6 to 12 and, more preferably, ranges from 4 to 8. In still another preferred embodiment, the R group of the silicone compound used to hydrophobize metal oxides is methyl, butyl, or octyl.

Any of a variety of metal oxides may be hydrophobized by the processes of this invention including zinc oxide, titanium dioxide, iron oxide, cesium oxide, zirconium oxide, silicon dioxide and antimony oxide. In a preferred embodiment, the metal oxides hydrophobized by the processes of this invention are those which have the ability to absorb ultraviolet radiation and, thus, are useful as sunscreen agents. Such metal oxides include, but are not limited to, zinc oxide, titanium dioxide, iron oxide, cesium oxide, zirconium oxide, and silicon dioxide.

The coated, hydrophobized metal oxides of this invention may be used in various formulations and compositions that are applied to the skin for protection from ultraviolet rays of the sun. Such formulations include sunscreen compositions and cosmetics.

This invention also provides methods of protecting the skin from ultraviolet rays of the sun which comprise contacting the skin with an effective protecting concentration of a hydrophobized metal oxide prepared according to processes described in this invention. An effective protecting concentration of a hydrophobized metal oxide is the amount necessary to achieve a desired SPF.

DETAILED DESCRIPTION OF THE INVENTION

Figure 1:
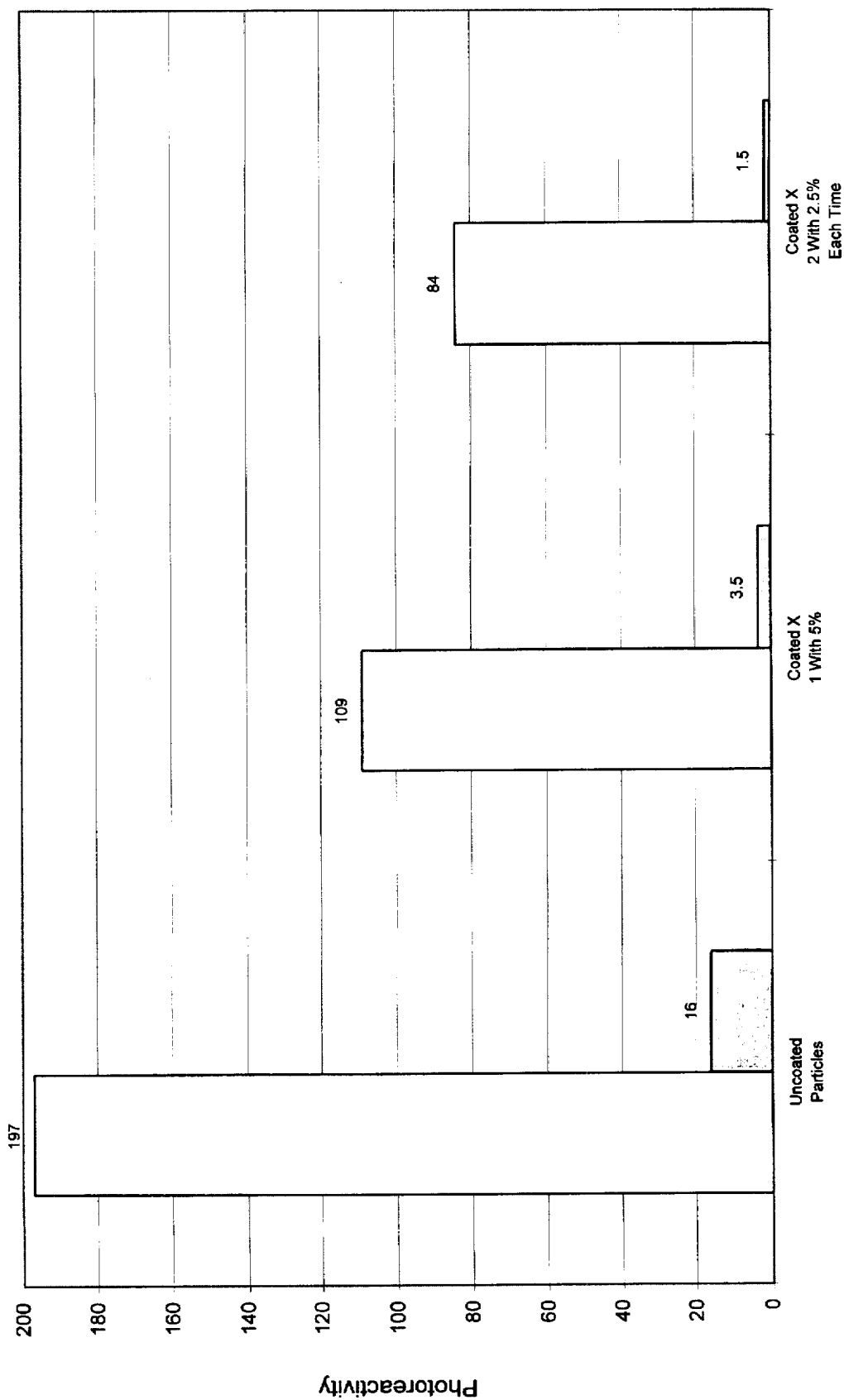
FIG. 1 is a bar graph that compares the relative photoreactivity of non-hydrophobized metal oxide particles (uncoated particles); singly-coated, hydrophobized metal oxide particles (coated×1 with 5%); and doubly-coated, hydrophobized metal oxide particles (coated×2 with 2.5% each time) prepared as described in Example 23. Zinc oxide particles (shaded bars), titanium dioxide particles (open bars).

It has been found that a highly effective system for hydrophobizing metal oxides, such as zinc oxide and titanium dioxide, makes use of a silicone compound conforming to the following structure:

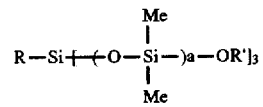

where Me is methyl;

R is alkyl having one to ten carbon atoms;

R' is methyl or ethyl;

a is an integer ranging from 4 to 12.

We have surprisingly learned that the value of the integer "a" in the structure is critical in developing a product which gives the desired hydrophobicity. The critical range is from 4 to 12. The value of a metal oxide, such as titanium dioxide, as a pigment is based upon its ability to remain dispersed and unreacted. For example, untreated titanium dioxide, placed into water, loses its effectiveness and good aesthetic qualities due to agglomeration. If the value of "a" is too low, the treated titanium dioxide is not sufficiently hydrophobic and its value as a pigment is destroyed. Making metal oxides, such as titanium dioxide, permanently hydrophobic by treatment with the correct silicone compound is highly desirable and heretofore has been very difficult to attain.

The silicone-coated, hydrophobized metal oxides of this invention are especially useful in many applications including as a sunscreen agent to prevent harmful effects of ultraviolet radiation from the sun. The compounds of the present invention are hydrophobic metal oxides which are prepared by the reaction of a silicone compound conforming to the following structure:

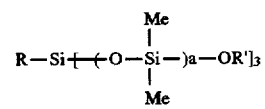

where Me is methyl,

R is alkyl having one to ten carbon atoms,

R' is methyl or ethyl, a is an integer ranging from 4 to 12, with a metal oxide.

The process for hydrophobizing a metal oxide comprises contacting the metal oxide with an effective hydrophobizing amount of a silicone compound having the formula:

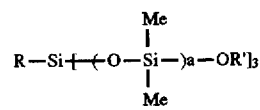

where Me is methyl,

R is alkyl having one to ten carbon atoms,

R' is methyl or ethyl, a is an integer ranging from 4 to 12, and heating the mixture of silicone compound and metal oxide to a temperature ranging from 40° C. to 100° C. for two to ten hours. The effective hydrophobizing amount is the amount necessary to result in particles of metal oxide which are coated with a desired percent by weight of the silicone compound. Preferably, the hydrophobized metal oxides of this invention are 0.1 to 25% by weight silicone compound. More preferably, the hydrophobized metal oxides are 0.5 to 25% by weight silicone compound and most preferably, the metal oxides are 1.0 to 10% by weight silicone compound.

In one embodiment of a process of this invention, the entire effective hydrophobizing amount of the silicone compound is contacted with the metal oxide at one time followed by heating. The metal oxides so produced are referred to as singly coated metal oxide and exhibit advantageously decreased photoreactivity and increased SPF compared to non-coated metal oxide.

The desirable characteristics of coating metal oxides with the silicone compound according to this invention can be further enhanced if the effective hydrophobizing amount of silicone compound is applied to the metal oxide by successive cycles of contacting a portion of the effective hydrophobizing amount of the silicone compound with the metal oxide followed by heating, and repeating such cycles of reacting the silicone compound with the metal oxide until the entire effective amount of silicone compound has been applied. For example, if the goal is to produce hydrophobized metal oxide particles containing a final percent by weight of silicone compound of 10%, a portion of the total effective hydrophobizing amount of silicone compound (e.g., ½) is contacted with the metal oxide and heated to first produce a coated metal oxide particle containing 5% silicone compound, followed by reacting the 5% silicone coated metal oxide particle with another portion (e.g., ¼) of the effective hydrophobizing amount of silicone compound to form a particle containing 7.5% silicone compound which, in turn, is reacted with the rest of the effective hydrophobizing amount of silicone compound (e.g., ¼) to produce a coated, hydrophobized metal oxide particle containing the desired 10% by weight silicone compound. Alternatively, a metal oxide particle containing 10% by weight silicone compound may be produced by reacting the silicone compound with the metal oxide in a different series of successive cycles of reacting portions of the effective hydrophobizing amount of silicone compound with metal oxide. For example, the coating may be applied in fractions of ⅒, ³⁄₁₀, ³⁄₁₀, ³⁄₁₀. Successive cycles of reaction yielding first a 1% silicone compound metal oxide, then a 4% silicone compound metal oxide, then a 7% silicone compound metal oxide and, finally, the desired 10% silicone compund metal oxide is one of many possible permutations of this aspect of the invention.

As another illustration, if the goal is to produce a hydrophobized metal oxide containing 20% by weight silicone compound, the coating may be applied in portions of ⅕, ⅕, ⅖, and ⅕. The successive cycles of reaction yielding a metal oxide containing 4% by weight silicone compound, then a metalo oxide containing 8% silicone compound, then a metal oxide, containing 16% silicone compound, and finally a metal oxide containing the desired 20% by weight silicone compound. In one alternative procedure, the 20% by weight silicone compound metal oxide particles are produced using two successive steps of reacting one-half of the effective hydrophobizing amount of silicone compound with metal oxide which first produces a 10% silicone compound metal oxide and then, in the second cycle, the desired 20% silicone compound metal oxide.

Thus, it should be understood by the above examples that the exact number of successive cycles used to produce a particular silicone coated, hydrobphobized metal oxide of this invention is determined by the skilled practitioner's judgment for allocating time and resources to produce a particular amount of a metal oxide containing a desired percent by weight silicone compound. Preferred successive coatings are in the range of two to ten successive coatings. In a preferred embodiment of this invention, the silicone compound is applied to the metal oxide in two successive cycles of contacting one-half of the effective hydrophobizing amount of silicone compound with the metal oxide followed by heating. Metal oxides coated with the silicone compound in this manner are referred to as doubly coated metal oxides.

While not wishing to be limited to a specific theory of why only specific silicone compounds of the present invention are effective, we believe that the placement of the reactive groups on the molecule have a dramatic effect upon the efficiency of hydrophobization.

The reaction by which hydrophobization occurs has been studied in detail using titanium dioxide as a representative metal oxide. The reaction by which hydrophobization occurs is one in which active sites on the metal oxide, in this case, titanium dioxide, react with the silicone to result in a covalent bond between silicone and titanium dioxide, and the formation of R'OH. The reaction is summarized as follows:

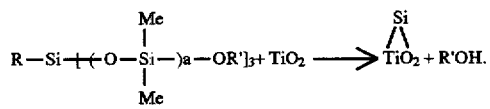

It should be clear from the above that the presence of three R' groups on the silicone compound can result in the formation of multiple bonds between silicone and the titanium dioxide crystals. Since no water is present in this process, the metal oxide crystals remain intact and "frozen" in shape by the silicone which acts like a matrix for the titanium dioxide crystals. The silicone preserves the structure of the titanium dioxide crystals, eliminates the reactivity in water, and makes them hydrophobic. This allows for the exposure of the hydrophobic titanium dioxide to water without deleterious effect to the titanium dioxide caused by the reactivity of the titanium dioxide in aqueous products. All these improvements are a direct unexpected result of modifying the surface of the titanium dioxide with a specific silicone compound, freezing the structure of the titanium oxide, hydrophobizing it, and removing the undesired reactivity.

When drawn out in its full structure, it becomes clear that the position of the R' groups can be varied by variation in "a". That is, as integer "a" increases, the distance between the R' groups increase and the three dimensional structure changes.

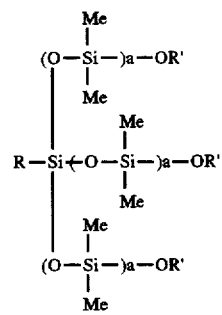

We have learned that the value of "a" is critical to the functionality of the hydrophobizing process. Specifically, if "a" is zero, the treated titanium dioxide does not maintain its structure when exposed to water. There is little effect upon the effectiveness of the hydrophobization until a value of about 4 is reached. The best performance is attained as "a"

approaches 8. As "a" is increased further, the silicone molecule becomes more hydrophobic and higher in molecular weight; this limits its effectiveness in coating the titanium dioxide. In effect, the reactive silicone is acting more like an oil than like a hydrophobizing agent, resulting in a titanium dioxide which is not covalently bonded to silicone. A noncovalent bond is easily removed by contact with water, resulting in agglomeration of the titanium dioxide, due to reactive groups present in the titanium dioxide, and silicone oil floating on the top of the aqueous formulation.

The production of R'OH as a byproduct in a dry process, as opposed to a slurry process, is very desirable. Another approach is the use of silicone compounds containing silanic hydrogen compounds of the structure Si-H, which results in the evolution of copious amounts of flammable hydrogen gas. In addition, the use of these kinds of compounds do not give the desired properties.

The hydrophobizing processes of this invention may also be used to coat metal oxides other than zinc oxide and titanium dioxide, including, but not limited to, iron oxide, cesium oxide, zirconium oxide, silicon dioxide, and antimony oxide, or combinations thereof. Particularly useful are metal oxides that are sunscreen agents, owing to their ability to absorb ultraviolet radiation. Such metal oxides having utility as sunscreen agents include, zinc oxide, titanium dioxide, iron oxide, cesium oxide, zirconium oxide, and silicon dioxide.

The coated, hydrophobized metal oxides of this invention may also be used in various combinations with other coated or uncoated metal oxides, for example, coated zinc oxide with coated or uncoated titanium dioxide particles. Such combinations may be provided in any selected ratio of coated/coated or coated/uncoated metal oxide, such as, 1:1, 1:3, 5:1, 10:1.

In a preferred embodiment the concentration of silicone compound in a silicone polymer coated hydrophobized metal oxide particle prepared according to this invention ranges from 0.1 to 30% by weight.

In another preferred embodiment the concentration of silicone compound in a silicone polymer coated hydrophobized metal oxide particle prepared according to this invention ranges from 0.5 to 20% by weight.

In another preferred embodiment the concentration of silicone compound in a silicone polymer coated hydrophobized metal oxide particle prepared according to this invention ranges from 1.0 to 10.0%.

In a preferred embodiment "a" is an integer ranging from 6 to 12.

In another preferred embodiment "a" is an integer ranging from 4 to 8.

In a preferred embodiment R is methyl.

In another preferred embodiment R is octyl.

In another preferred embodiment R is butyl.

In another preferred embodiment R is ethyl.

In a preferred embodiment, the process of the present invention is conducted at a temperature of between 80° and 100° C.

In another preferred embodiment, the process of the present invention is conducted at a temperature of between 90° and 100° C.

Testing For Sun Protection Factor (SPF)

It may be desirable to test a composition of the invention for its ability to protect the surface to which it is applied from ultraviolet radiation. Testing is particularly important for a composition which is useful for application to human skin, e.g., as a sunscreen or cosmetic composition. Sunscreens may be tested as described in the Federal Drug Administration guidelines entitled "Sunscreen Drug Products for Over-the-counter Human Use, Part II", 43 Fed. Reg. 166, 38259–38262 (Aug. 25, 1978) (hereby incorporated by reference). The testing procedure is as follows.

Sunscreen testing may be performed on human male or female volunteers. For inclusion in the test, the following criteria should be met. The subjects should be free of any dermatological or systemic disorder which would interfere with the results, e.g., no known abnormal response to sunlight, heat rash, chronic skin allergies, suntan or sunburn, etc. The subjects should not be under a doctor's care, or taking medication which may mask or interfere with the results. These determinations may be made by trained dermatological medical staff. The subjects should read, understand, and sign an informed consent document, as required by 21 C.F.R. 20. The panel of subject volunteers should be classified as a skin type I, II, or III defined according to 43 Fed. Reg. 38260 (1978) and as follows.

Type I—Always burns easily; never tans (sensitive)

Type II—Always burns easily; tans minimally (sensitive)

Types III—Burns moderately; tans gradually (light brown—normal).

The light source employed in the test is a 150 watt Xenon Arc Solar Simulator (Berger, D. S.: Specification and design of solar ultraviolet simulators. *J. Invest. Dermatol.* 53: 192–199 (1969), Solar Light Co., Philadelphia, Pa., Model 12S, Model 14S or Model 600) having a continuous emission spectrum in the ultraviolet B (UV-B) range from 290 to 320 nm. Xenon arc was selected on the basis of its black body radiation temperatures to 6000° K which produces continuous UV spectra (all wavelengths) substantially equivalent to that of natural sunlight. This devise is equipped with a dichroic mirror (which reflects all radiation below 400 nm) and works in conjunction with a 1 mm thick Schott WG-320 filter (which absorbs all radiation below 290 nm) to produce simulation of the solar ultraviolet A (UVA)-ultraviolet B (UVB) spectrum. A 1 mm thick UG 5 or UG 11 filter (black lens) is added to remove reflected (infra-red, greater than 700 nm) heat and remaining visible radiation.

UVB radiation may be monitored continuously during exposure using a Model DCS-1 Sunburn UV Meter/Dose Controller System (Solar Light Co.), formerly known as the Robertson-Berger Sunburn meter (R-B meter). Measurements are taken at a position within 8 mm from the surface of the skin. The field of irradiation is 1 cm in diameter. Realignment of the Light Sources and calibration of the sunburn meters should be conducted at list semiannually.

The SPF testing procedure is based on that described in the 43 Fed. Reg. 38264–38267 (1978). One test site area served to determine each subject's Minimal Erythema Dose (MED). This is executed by exposing the back to a series of timed incremental UV exposures at 25% intervals. The subject's smallest exposure or the least amount of energy required to produce erythema (MED) is the shortest time of exposure that produces minimally perceptible erythema at 20 to 24 hours post-irradiation. The test area is described as the infrascapular area of the back to the right and left of the midline. An 8% homosalate standard is delivered to the test site through a plastic volumetric syringe. This standard will give a uniform SPF of approximately 4–5.

The material is then evenly applied to a rectangular area measuring 5 cm×10 cm (50 cm$^2$) for a final concentration of 2.0 mg/cm$^2$. Fifteen (15.0) minutes after application, a series of UV light exposures in 25% increments, calculated from previously determined MEDs, bracketing the intended SPF is administered from the solar simulator to subsites within the treated area. On the actual day of testing, another series of exposures similar to the one given on the pervious day is administered to an adjacent untreated, unprotected area of the skin to re-determine the MED. Another adjacent test site is then selected to perform an SPF determination on the test substance.

Responses are evaluated as follows. Twenty to twenty-four hours post-exposure, the volunteers are evaluated for delayed erythemic response. The smallest exposure or the least amount of energy required to produce erythema (MED) in the treated site is recorded. The SPF is then calculated according to the following equations:

SPF=MED Protected Skin/MED Unprotected Skin. Results are rejected if the responses on the treated test site are randomly absent or out of sequence. This is an indication that the products are not spread uniformly. Results also are rejected if an MED could not be obtained due to elicited response at all exposure sites. If the exposure series failed to elicit an MED response on either the untreated or the applied skin areas, the test is then considered a technical failure and the subject's data is discarded.

The SPF of sunscreen formulations according to this invention will be in the range of 2 to 60, preferably 5 to 50, more preferably 10 to 30, and most preferably 15 to 20.

Testing For Photocatalytic Activity (Photoreactivity)

Photocatalytic activity, also called photoreactivity, refers to the ability of a compound to undergo degradation by exposure to light, such as UVA radiation. A standard assay to test specimens of the silicone coated, hydrophobized metal oxides of this invention for this photocatalytic activity is described below.

Each specimen is subjected to dispersion in analytical grade propan-2-ol (750 mg/l) sparged with pure oxygen for 10 minutes, and then exposed to a focused beam of UVA radiation for one hour with continuous stirring.

At the termination of the period of irradiation, approximately 10 ml of the reaction liquor are removed by syringe and the particular material separated by expelling the liquor through a MILLIPORE filter. The clarified liquor is then injected into a gas chromatograph fitted with a POROPAK Q column, and the propanone peak area obtained therefrom is compared to that of a pre-prepared standard solution of propanone in propan-2-ol.

It is known that the photoreaction is of zero order and, hence, the rate of production of propanone can be calculated to an accuracy of approximately 1%.

A more complete appreciation of this invention and the advantages thereof can be obtained from the following non-limiting examples.

EXAMPLES

Silicone Compounds

The silicone compounds useful for the preparation of the compounds of the present invention were provided by Siltech Inc. and conform to the following structures:

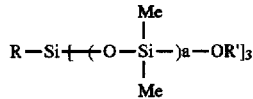

where Me is methyl;
R is alkyl having one to ten carbon atoms;
R' is methyl or ethyl;
a is an integer ranging from 4 to 12.

Silicone Compounds Useful for the Present Invention

The following are examples of materials which are compounds useful in treating the titanium dioxide according to our invention:

| Silicone Example | R | R' | a |
|---|---|---|---|
| 1 | $CH_3$ | $CH_3$ | 4 |
| 2 | $CH_3$ | $CH_2CH_3$ | 8 |
| 3 | $CH_3$ | $CH_3$ | 12 |
| 4 | $C_4H_9$ | $CH_3$ | 4 |
| 5 | $C_4H_9$ | $CH_2CH_3$ | 12 |
| 6 | $C_8H_{17}$ | $CH_3$ | 4 |
| 7 | $C_8H_{17}$ | $CH_2CH_3$ | 8 |

Silicone Compounds Not Useful for the Present Invention (For Comparison)

| Silicone Example | R | R' | a |
|---|---|---|---|
| 8 | $CH_3$ | $CH_3$ | 0 |
| 9 | $CH_3$ | $CH_2CH_3$ | 2 |
| 10 | $C_4H_9$ | $CH_3$ | 0 |
| 11 | $C_4H_9$ | $CH_2CH_3$ | 2 |

Titanium Dioxide

Titanium dioxide used in the preparation of the compounds of the present invention are commercially available from, SunSmart Inc.

The titanium dioxide used in the preparation of the products in the examples is SunSmart's T-Cote.

Process

The compounds of the present invention are prepared by contacting titanium dioxide with an effective hydrophobizing amount (preferably an amount to produce metal oxides containing silicone polymer ranging from 0.1% and 25% by weight) of a silicone which conforms to the following structure:

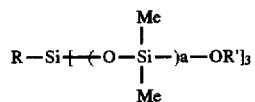

where Me is methyl;
R is alkyl having one to ten carbon atoms;
R' is methyl or ethyl;
a is an integer ranging from 4 to 12;
then heating the intermediate to a temperature of between 40° C. and 100° C. for between 2 hr and 10 hr. During this time alcohol is removed. The reaction is considered complete when 97% of the theoretical alcohol is removed. The quantity of alcohol removed is considered more important than the time at which the material is held at temperature.

When R' is CH3, the alcohol removed is methanol. When R' is CH2CH3 the alcohol removed is ethanol.

The titanium dioxide is coated dry. The silicone can be applied by simply mixing it with the titanium dioxide, or in a preferred method using traditional methods for applying liquids to solids like a "V" blender.

Example 12

To 90.0 grams of titanium dioxide is added an effective hydrophobizing amount of 10.0 grams of silicone Example #1. The powder is then mixed well. The powder is then placed in an oven and heated to 80° C. for 6 hr. During this time alcohol is removed. The reaction is considered complete when 97% of the theoretical alcohol is removed. The amount of alcohol removed is determined by weighing the contained.

Examples 13–22

Example 12 is repeated only this time the specified effective hydrophobizing amount of the specified silicone is added in place of the 10 grams of silicone Example 1 and the specified number of grams of titanium dioxide are used.

| Compounds of the Present Invention | | |
|---|---|---|
| Example | Silicone Compound Example/Grams | Titanium dioxide Grams |
| 13 | 2 | 25.0 | 75.0 |
| 14 | 3 | 1.0 | 99.0 |
| 15 | 4 | 5.0 | 95.0 |
| 16 | 5 | 10.0 | 90.0 |
| 17 | 6 | 0.1 | 99.1 |
| 18 | 7 | 10.0 | 90.0 |
| 19 | 8 | 25.0 | 75.0 |
| 20 | 9 | 1.0 | 99.0 |
| 21 | 10 | 5.0 | 95.0 |
| 22 | 11 | 10.0 | 90.0 |

Applications Results (a) Viscosity in Formulations

The viscosity of a dispersion of titanium dioxide in octyl palmitate is also an indication of the effectiveness of the treatment of titanium dioxide. Particles which are effectively treated do not swell in oil. The more the titanium dioxide swells the higher the viscosity of a dispersion.

The following test formula was evaluated:

| % Weight | Material |
|---|---|
| 33.0 | titanium dioxide |
| 67.0 | Octyl Palmitate |
| 100.0 | |

The dispersions were made using a sonic probe 100 watts at 50% power. The viscosity was measured using a Brookfield Viscometer. Again the higher the viscosity, the greater the oil swell and the less efficient the coating.

| Test Material | Viscosity in formulation |
|---|---|
| Example 19 | 440 cps |
| Example 22 | 410 cps |
| Example 21 | 500 cps |
| Untreated TiO$_2$ | 960 cps |

The lower the viscosity, the more effective the surface treatment.

(b) Stability in Aqueous Vitamin C

As noted above, untreated TiO$_2$ will react with an aqueous solution of vitamin C to produce a yellow color. The more intense the color, the greater the reactivity of the TiO$_2$. This offers a good analytical test for effectiveness of the treatment method.

Method 5.0 grams of the test TiO$_2$ is added to 5 grams of a 1% weight/weight solution of vitamin C in water. 0.05 grams of dioctylsulfosuccinate is then added to speed up the wetting of the TiO$_2$. The resultant slurry is mixed with a magnetic stirrer for 10 minutes. 5 grams of a 2% weight/weight solution of xanthan gum in water is added under agitation. This results in a thick slurry which can be drawn into a film on a glass plate. The slurry is drawn down on Form 3NT-3 ink test coat book paper from Leneta Co in Hohokus N.J., using a #22 wire wound dry down bar. The film is allowed to dry 1 hour. The color of the resultant film is measured using an X-rite model 418 reflectance densitometer on the white yellow filter. Four films are cast for each product evaluated.

| | Untreated TiO$_2$ | Ex. 19 | Ex. 22 | Background |
|---|---|---|---|---|
| Test 1 | 0.20 | 0.17 | 0.17 | 0.16 |
| Test 2 | 0.19 | 0.16 | 0.17 | 0.15 |
| Test 3 | 0.21 | 0.17 | 0.16 | 0.15 |
| Test 4 | 0.19 | 0.16 | 0.17 | 0.15 |
| Average | 0.1975 | 0.165 | 0.17 | 0.15 |

The background is subtracted from the measurement for a yellowing measurement.

| | Untreated TiO$_2$ | Ex. 19 | Ex. 22 |
|---|---|---|---|
| Average | 0.1975 | 0.165 | 0.17 |
| Average − Background | 0.0475 | 0.015 | 0.02 |

The untreated is over 3 times more yellow than Example 19 and 2 times more yellow than Example 22. The reduction in reactivity is a demonstration of the effectiveness of the coating.

The hydrophobized titanium dioxide is used in a variety of applications and formulations. These applications include personal care sun screen applications.

Metal Oxide Compositions

A particular species of coated metal oxide of this invention may be combined with other species of coated or non-coated metal oxides to form compositions that exhibit the qualities of the various metal oxide species. For example, a hydrophobized titanium dioxide of this invention may be combined with a hydrophobized iron oxide and/or a non-coated zinc oxide and used in a sunscreen or cosmetic formulation.

Coated metal oxides of the invention may also be provided in admixture with (i.e., uniformly dispersed within) pharmaceutically acceptable biocompatible ingredients which may include water, inorganic pigments, organic pigments, emulsifiers, oil soluble sunscreens, water soluble sunscreens, alpha hydroxy acids, dispersants, oil soluble vitamins, water soluble vitamins, waxes, silicone, and combinations thereof.

Example 23

In this example, titanium dioxide and zinc oxide were coated with the silicone compound in a manner similar to that used to produce the hydrophobized, singly coated metal oxides of Examples 12 to 22, described above, except that the total amount of silicone compound that was to be applied to the metal oxide (the hydrophobizing amount) was divided into two equal portions and each portion applied in two successive cycles of contacting each portion of silicone compound to the metal oxide followed by heating. Metal oxide particles produced by two successive steps of silicone application are referred to as doubly coated metal oxides.

The bar graph in FIG. 1 shows the relative photoreactivity of titanium dioxide (open bar) and zinc oxide (shaded bar) particles treated in various ways: not hydrophobized (uncoated particles); hydrophobized in one step (singly coated) to contain a total of 5% by weight silicone compound (coated×1 with 5%); and hydrophobized to contain a total of 5% by weight silicone compound in two successive steps (doubly coated) at 2.5% by weight per step (coated×2 with 2.5% each time). Singly coated titanium dioxide exhibited a decreased photoreactivity compared to untreated titanium dioxide, i.e., from a relative measurement of 197 (untreated) to 109 (singly coated). Doubly coated titanium dioxide exhibited an even greater decrease in relative photoreactivity from 197 (untreated) to 84. A similar improvement was seen in the case of zinc oxide where the relative photoreactivity was decreased from 16 for untreated particles to 3.5 for singly coated particles and 1.5 for doubly coated particles.

Other Embodiments

While the invention has been described in detail and with reference to specific embodiments thereof, it will be apparent to one skilled in the art that various changes and modifications can be made therein without departing from the spirit and scope thereof.

Other embodiments of the invention are found within the following claims.

We claim:

1. A hydrophobic metal oxide coated with a silicone compound which is prepared by the reaction of the silicone compound having the structure:

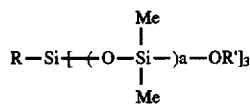

wherein, Me is methyl,
R is alkyl having one to ten carbon atoms,
R' is methyl or ethyl,
a is an integer ranging from 4 to 12, with the metal oxide.

2. The hydrophobic metal oxide of claim 1 wherein the concentration of silicone compound ranges from 0.1 to 25% by weight.

3. The hydrophobic metal oxide of claim 1 wherein the concentration of silicone compound ranges from 0.5 to 20% by weight.

4. The hydrophic metal oxide of claim 1 wherein the concentration of silicone compound ranges from 1.0 to 10% by weight.

5. The hydrophobic metal oxide of claim 1 wherein a is an integer ranging from 6 to 12.

6. The hydrophobic metal oxide of claim 1 wherein a is an integer ranging from 4 to 8.

7. The hydrophobic metal oxide of claim 1 wherein R is selected from the group consisting methyl, butyl, and octyl.

8. The hydrophobic metal oxide of claim 1 wherein the metal oxide is selected from the group consisting of zinc oxide, titanium dioxide, iron oxide, cesium oxide, zirconium oxide, silicon dioxide, and antimony oxide.

9. A process for hydrophobizing a metal oxide comprising contacting the metal oxide with an effective hydrophobicizing amount of a silicone compound having the formula:

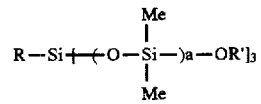

wherein, Me is methyl,
R is alkyl having one to ten carbon atoms,
R' is methyl or ethyl,
a is an integer ranging from 4 to 12,
and heating the mixture to a temperature between 40° C. and 100° C. for two to ten hours.

10. The process for hydrophobizing a metal oxide according to claim 9, wherein the process consists of:
(a) applying a portion of the effective hydrophobizing amount of the silicone compound to the metal oxide;
(b) heating the mixture of step (a) to a temperature between 40° C. and 100° C. for two to ten hours; and
(c) repeating steps (a) and (b) until the metal oxide has been contacted with the entire effective amount of the silicone compound.

11. The process for hydrophobizing a metal oxide according to claim 9, wherein the metal oxide is contacted with the entire effective hydrophobizing amount of the silicone compound a t one time prior to heating.

12. The process for hydrophobizing a metal oxide according to claims 10 or 11, wherein the metal oxide is selected from the group consisting of zinc oxide, titanium dioxide, iron oxide, cesium oxide, zirconium oxide, silicon dioxide, and antimony oxide.

13. The process for hydrophobizing a metal oxide according to claims 10 or 11, wherein the effective hydrophobicizing concentration of silicone compound ranges from 0.1 to 20% by weight.

14. The process for making a hydrophobic metal oxide according to claims 10 or 11, wherein the effective hydrophobicizing concentration of silicone compound ranges from 0.5 to 20% by weight.

15. The process for making a hydrophobic metal oxide according to claims 10 or 11, wherein the effective hydrophobicizing concentration of silicone compound ranges from 1.0 to 10% by weight.

16. The process for making a hydrophobic metal oxide according to claims 10 or 11, wherein a is an integer ranging from 6 to 12.

17. The process for making a hydrophobic metal oxide according to claims 10 or 11, wherein a is an integer ranging from 4 to 8.

18. The process for making a hydrophobic metal oxide according to claims 10 or 11, wherein R is selected from the group consisting of methyl, butyl, and octyl.

19. A hydrophobized metal oxide prepared according to the process of claim 10.

20. The hydrophobized metal oxide according to claim 19 selected from the group consisting of zinc oxide, titanium dioxide, iron oxide, cesium oxide, zirconium oxide, silicon dioxide, and antimony oxide.

21. A hydrophobized metal oxide prepared according to the process of claim 11.

22. The hydrophobized metal oxide according to claim 21 selected from the group consisting of zinc oxide, titanium dioxide, iron oxide, cesium oxide, zirconium oxide, silicon dioxide, and antimony oxide.

23. A method of protecting the skin from the ultraviolet rays of the sun comprising contacting the skin with an effective protecting concentration of a hydrophobized metal oxide prepared by a process for hydrophobizing a metal oxide comprising contacting the metal oxide with an effective hydrophobicizing concentration of a silicone compound having the formula:

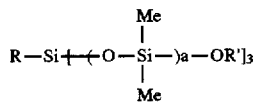

wherein, Me is methyl,
R is alkyl having one to ten carbon atoms,
R' is methyl or ethyl,
a is an integer ranging from 4 to 12,
and heating the mixture to a temperature between 40° C. and 100° C. for two to ten hours.

24. The method of protecting the skin from the ultraviolet rays of the sun comprising contacting the skin with an effective protecting concentration of a hydrophobized metal oxide according to claim 23, wherein the process for hydrophobizing the metal oxide consists:
(a) applying a portion of the effective hydrophobizing amount of the silicone compound to the metal oxide;
(b) heating the mixture of step (a) to a temperature between 40° C. and 100° C., for two to ten hours; and
(c) repeating steps (a) and (b) until the entire effective concentration of the silicone compound has been used.

25. The method of protecting the skin from the ultraviolet rays of the sun comprising contacting the skin with an effective protecting concentration of a hydrophobized metal oxide according to claim 23, wherein the process for hydrophobizing the metal oxide consists of contacting the metal oxide with the entire effective hydrophobizing amount of the silicone compound at one time prior to heating.

26. The method of protecting the skin from the ultraviolet rays of the sun according to claims 23, wherein the metal oxide is selected from the group consisting of zinc oxide, titanium dioxide, iron oxide, cesium oxide, zirconium oxide, silicon dioxide, and antimony oxide.

27. The method of claim 23 wherein said effective protecting concentration ranges between 0.1% and 25% by weight.

28. The method of claim 23 wherein a is an integer ranging from 6 to 12.

29. The method of claim 23 wherein a is an integer ranging from 4 to 8.

30. The method of claim 23 wherein R is methyl.

31. A composition comprising the hydrophobic metal oxide of claim 1 in admixture with a pharmaceutically acceptable ingredient.

32. A composition according to claim 31 wherein the metal oxide is selected from the group consisting of zinc oxide, titanium dioxide, iron oxide, cesium oxide, zirconium oxide, silicon dioxide, and antimony oxide.

33. The composition according to claim 31 wherein the pharmaceutically acceptable ingredient is selected from the group consisting of water, inorganic pigments, organic pigments, emulsifiers, oil soluble sunscreens, water soluble sunscreens, alpha hydroxy acids, dispersants, oil soluble vitamins, water soluble vitamins, waxes, silicone, and combinations thereof.

34. The composition according to claim 31 wherein the composition confers a sun protection factor in the range of 2 to 60.

35. The composition according to claim 31 further comprising a second different coated hydrophobic metal oxide of claim 1.

36. The composition according to claim 31 further comprising a second different metal oxide.

37. The composition according to claim 35 or 36 wherein the metal oxide is selected from the group consisting of zinc oxide, titanium dioxide, iron oxide, cesium oxide, zirconium oxide, silicon dioxide, and antimony oxide.

38. A hydrophobic metal oxide containing a first coat and second coat of a silicone compound having the formula:

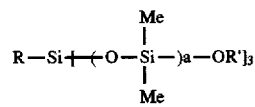

wherein, Me is methyl,
R is alkyl having one to ten carbon atoms,
R' is methyl or ethyl, and
a is an integer ranging from 4 to 12.

39. The hydrophobic metal oxide of claim 38 wherein the concentration of silicone compound ranges from 0.1 to 25% by weight.

40. The hydrophobic metal oxide of claim 38 wherein the concentration of silicone compound ranges from 0.5 to 20% by weight.

41. The hydrophic metal oxide of claim 38 wherein the concentration of silicone compound ranges from 1.0 to 10% by weight.

42. The hydrophobic metal oxide of claim 38 wherein a is an integer ranging from 6 to 12.

43. The hydrophobic metal oxide of claim 38 wherein a is an integer ranging from 4 to 8.

44. The hydrophobic metal oxide of claim 38 wherein R is selected from the group consisting of methyl, butyl, and octyl.

45. The hydrophobic metal oxide of claim 38 wherein the metal oxide is selected from the group consisting of zinc oxide, titanium dioxide, iron oxide, cesium oxide, zirconium oxide, silicon dioxide, and antimony oxide.

46. A composition comprising the hydrophobic metal oxide of claim 38 in admixture with a pharmaceutically acceptable ingredient.

47. A composition according to claim 46 wherein the metal oxide is selected from the group consisting of zinc oxide, titanium dioxide, iron oxide, cesium oxide, zirconium oxide, silicon dioxide, and antimony oxide.

48. The composition according to claim 46 wherein the pharmaceutically acceptable ingredient is selected from the group consisting of water, inorganic pigments, organic pigments, emulsifiers, oil soluble sunscreens, water soluble sunscreens, alpha hydroxy acids, dispersants, oil soluble vitamins, water soluble vitamins, waxes, silicone, and combinations thereof.

49. The composition according to claim 46 wherein the composition confers a sun protection factor of 2 to 60.

50. The composition according to claim 46 further comprising a second different hydrophobic metal oxide of claims 31.

51. The composition according to claims 46 further comprising a second different metal oxide.

52. The composition according to claim 50 or 51 wherein the metal oxide is selected from the group consisting of zinc oxide, titanium dioxide, iron oxide, cesium oxide, zirconium oxide, silicon dioxide, and antimony oxide.

* * * * *